United States Patent
Takahashi

(10) Patent No.: US 8,853,473 B2
(45) Date of Patent: Oct. 7, 2014

(54) AZEOTROPIC OR AZEOTROPE-LIKE COMPOSITION AND PROCESS FOR PRODUCING 2,3,3,3-TETRAFLUOROPROPENE

(75) Inventor: Kazuhiro Takahashi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 202 days.

(21) Appl. No.: 13/060,869

(22) PCT Filed: Aug. 21, 2009

(86) PCT No.: PCT/JP2009/065023
§ 371 (c)(1),
(2), (4) Date: Feb. 25, 2011

(87) PCT Pub. No.: WO2010/024366
PCT Pub. Date: Mar. 4, 2010

(65) Prior Publication Data
US 2011/0160500 A1    Jun. 30, 2011

Related U.S. Application Data

(60) Provisional application No. 61/091,783, filed on Aug. 26, 2008.

(51) Int. Cl.
C07C 17/00 (2006.01)
C07C 21/00 (2006.01)
C07C 17/38 (2006.01)
C07C 21/18 (2006.01)
C07C 17/383 (2006.01)

(52) U.S. Cl.
CPC ............... *C07C 21/18* (2013.01); *C07C 17/383* (2013.01)
USPC ........................... 570/178; 570/175; 570/177

(58) Field of Classification Search
None
See application file for complete search history.

(56) References Cited

U.S. PATENT DOCUMENTS

| 7,476,771 B2 | 1/2009 | Miller et al. |
| 2007/0100175 A1 | 5/2007 | Miller et al. |
| 2007/0197842 A1* | 8/2007 | Mukhopadhyay et al. ... 570/155 |
| 2010/0162738 A1 | 7/2010 | Low et al. |

FOREIGN PATENT DOCUMENTS

| WO | 2007/053736 | 5/2007 |
| WO | 2007/144632 | 12/2007 |
| WO | 2008/030440 | 3/2008 |

OTHER PUBLICATIONS

International Search Report issued Dec. 2, 2010 in International (PCT) Application No. PCT/JP2009/065023.
PCT Written Opinion of the International Searching Authority issued Dec. 2, 2010 in International (PCT) Application No. PCT/JP2009/065023.

* cited by examiner

*Primary Examiner* — Clinton Brooks
(74) *Attorney, Agent, or Firm* — Wenderoth, Lind & Ponack, L.L.P.

(57) ABSTRACT

The present invention provides a process for producing 2,3,3,3-tetrafluoropropene, comprising distilling a mixture of water and 2,3,3,3-tetrafluoropropene to separate the mixture into a first stream and a second stream, the first stream containing 2,3,3,3-tetrafluoropropene with a water content higher than the original mixture, and the second stream containing 2,3,3,3-tetrafluoropropene with a water content lower than the original mixture; and obtaining 2,3,3,3-tetrafluoropropene with a reduced water content from the second stream. The process of the invention can efficiently remove water from 2,3,3,3-tetrafluoropropene (HFO-1234yf).

6 Claims, 2 Drawing Sheets

AZEOTROPIC OR AZEOTROPE-LIKE COMPOSITION AND PROCESS FOR PRODUCING 2,3,3,3-TETRAFLUOROPROPENE

This application claims priority based on U.S. Provisional Application No. 61/091,783 filed Aug. 26, 2008.

TECHNICAL FIELD

The present invention relates to an azeotropic or azeotrope-like composition comprising 2,3,3,3-tetrafluoropropene and water, and a process for producing 2,3,3,3-tetrafluoropropene with a reduced water content by utilizing the properties of the azeotropic or azeotrope-like composition.

BACKGROUND ART

Alternative refrigerants such as HFC-125 ($C_2HF_5$) and HFC-32 ($CH_2F_2$) have been widely used as important replacements for CFC, HCFC, etc. that cause ozone layer depletion. However, these alternative refrigerants are potent global warming substances, thus creating concern that diffusion of the refrigerants would enhance global warming. As a preventive measure, these refrigerants are recovered after use. However, complete recovery of the refrigerants is impossible. In addition, the diffusion of said refrigerants due to leakage, etc. cannot be ignored. The use of $CO_2$ or hydrocarbon-based substances as alternative refrigerants has also been investigated. However, because $CO_2$ refrigerants have low efficiency, devices using such refrigerants inevitably become large. Thus, $CO_2$ refrigerants have many problems in terms of the overall reduction of greenhouse gas emissions, including energy to be consumed. Furthermore, hydrocarbon substances pose safety problems due to their high flammability. 2,3,3,3-tetrafluoropropene (HFO-1234yf, $CF_3CF=CH_2$), which is a olefinic HFC having a low global warming potential, has recently been attracting attention as a material to solve the above problems.

A known method for producing 2,3,3,3-tetrafluoropropene (HFO-1234yf) comprises subjecting 1,1,1,2,3-pentafluoropropane (HFC-245eb) or 1,1,1,2,2-pentafluoropropane (HFC-245cb) to a dehydrofluorination reaction. However, when such a dehydrofluorination method is used, HFO-1234yf is obtained as a mixture of HFO-1234yf with HF, and it is thus necessary to remove HF by using some method.

The simplest method for removing HF from a mixture of HFO-1234yf and HF is using water to absorb HF. However, HFO-1234yf treated by this method is always intermixed with steam mist, or water in an amount corresponding to the vapor pressure. There are also various other sources of water, such as water contained in the starting materials, water derived from the catalyst, and water remaining in the equipment. Thus, the obtained HFO-1234yf is intermixed with these waters.

The water contained in the final product HFO-1234yf affects the performance of HFO-1234yf as a refrigerant, as well as its stability and corrosivity to the device. Therefore, the removal of water is an important factor in quality control, and a method for removing water is a particularly important technique.

A common method for removing water is the use of an adsorbent, such as a molecular sieve. For example, Patent Literature (PTL) 1 listed below discloses a method comprising drying liquid HFO-1234yf over zeolite. However, this method requires the high-speed treatment of a gas having a comparatively low water content, thus necessitating the use of a large dehydrating tower. Furthermore, periodic reactivation or replacement of the adsorbent is also necessary, and industrial waste is generated in large amounts during the replacement of the adsorbent.

CITATION LIST

Patent Literature

PTL 1: WO 2007/144632

SUMMARY OF INVENTION

Technical Problem

The present invention was made in view of the above prior art problems. A primary object of the invention is to provide a method for efficiently removing water from 2,3,3,3-tetrafluoropropene (HFO-1234yf).

Solution to Problem

The present inventors carried out extensive research to achieve the above object. As a result, the inventors discovered an unknown phenomenon that 2,3,3,3-tetrafluoropropene and water form a minimum boiling point azeotropic composition (an azeotropic composition wherein liquid-liquid separation occurs is referred to as a heterogeneous azeotropic composition). Further, the inventors found that water can be efficiently removed from 2,3,3,3-tetrafluoropropene by utilizing the azeotropic property. The present invention has been accomplished based on this finding.

More specifically, the present invention provides the following azeotropic or azeotrope-like composition, and process for producing 2,3,3,3-tetrafluoropropene having a reduced water content.

1. An azeotropic or azeotrope-like composition comprising 2,3,3,3-tetrafluoropropene and water.

2. An azeotropic or azeotrope-like composition comprising 99 to 99.995 wt. % of 2,3,3,3-tetrafluoropropene and 0.005 to 1 wt. % of water.

3. A process for producing 2,3,3,3-tetrafluoropropene, comprising distilling a mixture of water and 2,3,3,3-tetrafluoropropene to separate the mixture into a first stream and a second stream, the first stream containing 2,3,3,3-tetrafluoropropene with a water content higher than that of the original mixture, and the second stream containing 2,3,3,3-tetrafluoropropene with a water content lower than that of the original mixture;

and obtaining 2,3,3,3-tetrafluoropropene with a reduced water content from the second stream.

4. The process for producing 2,3,3,3-tetrafluoropropene according to item 3, wherein the distillation is performed at a pressure in the range of atmospheric pressure to 2 MPa.

5. The process for producing 2,3,3,3-tetrafluoropropene according to item 3 or 4, further comprising cooling the mixture of the first stream obtained by separation in item 3 or 4 so that the mixture separates into a liquid phase A with a high water content and a liquid phase B with a high 2,3,3,3-tetrafluoropropene content.

6. The process for producing 2,3,3,3-tetrafluoropropene according to item 5, further comprising recycling the liquid phase B obtained by separation in item 5 to a distillation column.

The azeotropic or azeotrope-like composition of the present invention and the process for producing 2,3,3,3-tetrafluoropropene are described below in more detail.

Azeotropic or Azeotrope-Like Composition

The azeotropic or azeotrope-like composition of the present invention comprises 2,3,3,3-tetrafluoropropene and water.

As a result of the research of the present inventors, they discovered the following phenomenon: when a mixture of 2,3,3,3-tetrafluoropropene and water is rectified, the water content of the mixture increases toward the top of the rectification column; however, once the water content has reached a certain level, no further increase of water content is observed. This result reveals that 2,3,3,3-tetrafluoropropene and water form a minimum boiling point azeotropic composition. The specific azeotropic composition varies depending on the temperature and pressure. For example, when the pressure is 0.55 MPa and the temperature is 16° C., the composition consisting of 99.979 wt. % of 2,3,3,3-tetrafluoropropene and 0.021 wt. % of water is an azeotropic composition.

In the present invention, the pressure to be applied in distillation to remove water is preferably in the range of atmospheric pressure to 2 MPa, as described below. When the pressure is within this range, a mixture of about 99 to about 99.995 wt. % of 2,3,3,3-tetrafluoropropene and about 0.005 to about 1 wt. % of water forms an azeotropic or azeotrope-like composition.

The term "azeotropic composition" as used herein refers to a mixture wherein the vapor phase in equilibrium with the liquid phase has a composition identical to that of the liquid phase. The azeotrope-like composition as used herein refers to a mixture wherein the vapor phase in equilibrium with the liquid phase has a composition similar to that of the liquid phase.

Process for Producing 2,3,3,3-Tetrafluoropropene with a Reduced Water Content

According to the process of the present invention for producing 2,3,3,3-tetrafluoropropene, a mixture of 2,3,3,3-tetrafluoropropene and water is first distilled. The distillation may be performed at a pressure in the range of atmospheric pressure (0.1013 MPa) to about 2 MPa. An overly low pressure results in a low reflux temperature, and liquid-liquid phase separation may occur in the distillation column. Therefore, the distillation is preferably performed at a pressure in the range of about 0.4 to about 2 MPa.

Although the water content of the starting HFO-1234yf is not particularly limited, there is a limit to the mutual solubility of HFO-1234yf and water. If the water content of the starting HFO-1234yf is too high, liquid-liquid separation may occur in the rectification column, which results in a three-phase distillation, thus reducing the efficiency of the column. Accordingly, before feeding into the rectification column, a decanter, etc. may be used to separate the starting HFO-1234yf into an aqueous phase and an HFO-1234yf-rich organic phase to reduce the water content of HFO-1234yf somewhat, and then HFO-1234yf with a reduced water content may be fed into the rectification column.

As described above, when the pressure is in the range of atmospheric pressure (0.1013 MPa) to 2 MPa, a mixture of 99 wt. % to 99.995 wt. % of 2,3,3,3-tetrafluoropropene and about 0.005 to about 1 wt. % of water, i.e., a mixture having a water content of 50 to 10,000 ppm (expressed by weight; the same hereinafter) forms an azeotropic or azeotrope-like composition.

Accordingly, when a mixture of water and 2,3,3,3-tetrafluoropropene having a water content lower than that of the azeotropic composition is distilled, a mixture of water and 2,3,3,3-tetrafluoropropene with a concentrated water, i.e., a mixture of water and 2,3,3,3-tetrafluoropropene whose water content is higher than that of the original mixture fed to the distillation column can be obtained from the top of the column.

When an adsorbent such as a molecular sieve is used to dry the mixture of water and 2,3,3,3-tetrafluoropropene with a concentrated water obtained from the top of the column, the drying tower to be used can be downsized compared to conventional methods. When the mixture of 2,3,3,3-tetrafluoropropene and water obtained from the top of the column is cooled using a decanter or the like to separate the mixture into a liquid phase A with a high water content and a liquid phase B with a high 2,3,3,3-tetrafluoropropene content, water can be more efficiently removed. When using a decanter, the mixture may be separated into two liquid phases by cooling to a temperature lower than the temperature of the mixture of 2,3,3,3-tetrafluoropropene and water withdrawn from the distillation column. The cooling temperature may be a temperature at which the water obtained by the liquid-liquid separation does not freeze.

Water can be efficiently removed by performing the distillation and liquid-liquid separation as a continuous operation.

The phase with a high water content obtained by separation according to the above method may be discarded. The phase with a high 2,3,3,3-tetrafluoropropene content may be returned to the distillation column and distilled again, or may be singly dried over a molecular sieve to remove water, thus enabling the drastic downsizing of the drying tower.

The 2,3,3,3-tetrafluoropropene with a reduced water content obtained from the bottom of the column can also dried over a molecular sieve or the like to remove water, thus enabling the removal of water using a small drying tower.

According to the above method, 2,3,3,3-tetrafluoropropene with a reduced water content can be obtained from a mixture of 2,3,3,3-tetrafluoropropene and water.

When 2,3,3,3-tetrafluoropropene and water are distilled, the distillate may contain impurities contained in 2,3,3,3-tetrafluoropropene, such as remaining unreacted 1,1,1,2,3-pentafluoropropane (HFC-245eb) and 1,1,1,2,2-pentafluoropropane (HFC-245cb) charged as starting materials for the dehydrofluorination reaction. In that case, the impurities may be withdrawn together with 2,3,3,3-tetrafluoropropene from the distillation column and removed by separation using another distillation column.

The terms "concentrated" and "removed" are used herein to refer to opposing concepts. More specifically, concentrating a specific component in a mixture means removing the components other than the specific component from the mixture.

Advantageous Effects of Invention

According to the process of the present invention, water-containing 2,3,3,3-tetrafluoropropene obtained by various synthesizing methods is subjected to distillation utilizing the azeotropic properties of 2,3,3,3-tetrafluoropropene and water, and optionally further subjected to liquid-liquid separation to efficiently remove water, whereby 2,3,3,3-tetrafluoropropene with a reduced water content can be easily produced.

DESCRIPTION OF EMBODIMENTS

Examples are given below to illustrate the present invention in more detail.

Example 1

Figure 1:
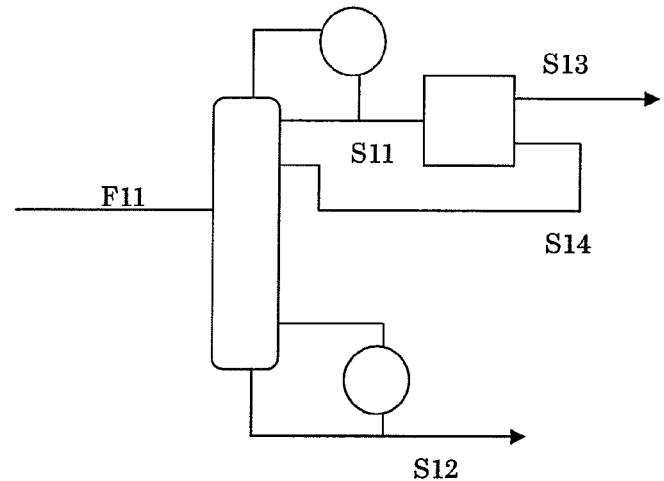
FIG. 1 is a flow chart outlining the steps of the method in Example 1.

Water was removed from 2,3,3,3-tetrafluoropropene according to the flow chart shown in FIG. 1. Each of Examples 1 to 3 below illustrates a process in which distillation and liquid-liquid separation were performed as a continuous operation.

First, 2,3,3,3-tetrafluoropropene containing 50 ppm of water was fed to an intermediate tray of a rectification column 2 m in height and 7 cm in diameter at a rate of 10 kg/hr (stream F11), and rectified under the following conditions: column operating pressure: 0.6 MPa; column top temperature: 21° C.; reflux ratio: 16.

2,3,3,3-tetrafluoropropene with an increased water content was withdrawn from the top of the column and fed to a decanter at a rate of 1 kg/hr (Stream S11). By cooling to 2° C., liquid-liquid phase separation was allowed to proceed. The lower layer was returned to the top of the column (Stream S14), and the upper layer was isolated as a water-rich layer (Stream S13).

2,3,3,3-tetrafluoropropene with a reduced water content (Stream S12) was obtained from the bottom of the column at a rate of 9 kg/hr.

Table 1 below shows the results of measuring the water content of each stream by a Karl Fischer moisture meter.

TABLE 1

| Water content (by weight) | | | | |
|---|---|---|---|---|
| F11 | S11 | S12 | S13 | S14 |
| 50 ppm | 200 ppm | 3 ppm | 90% | 30 ppm |

Example 2

Figure 2:
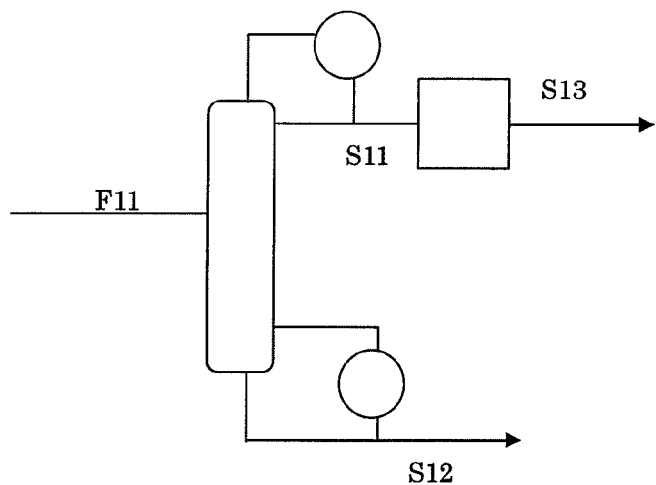
FIG. 2 is a flow chart outlining the steps of the method in Example 2.

Water was removed from 2,3,3,3-tetrafluoropropene according to the flow chart shown in FIG. 2.

First, 2,3,3,3-tetrafluoropropene containing 50 ppm of water was fed to an intermediate tray of a rectification column 2 m in height and 7 cm in diameter at a rate of 10 kg/hr (Stream F11), and rectified under the following conditions: column operating pressure: 0.6 MPa; column top temperature: 21° C.; reflux ratio: 16.

2,3,3,3-tetrafluoropropene with an increased water content was withdrawn from the top of the column at a rate of 1 kg/hr (Stream S11), fed to a drying tower containing a molecular sieve, and dried (Stream S13).

2,3,3,3-tetrafluoropropene with a reduced water content was obtained from the bottom of the column at a rate of 9 kg/hr (Stream S12).

Table 2 below shows the results of measuring the water content of each stream by a Karl Fischer moisture meter.

TABLE 2

| Water content (by weight) | | | |
|---|---|---|---|
| F11 | S11 | S12 | S13 |
| 50 ppm | 200 ppm | 3 ppm | 5 ppm |

Example 3

Figure 3:
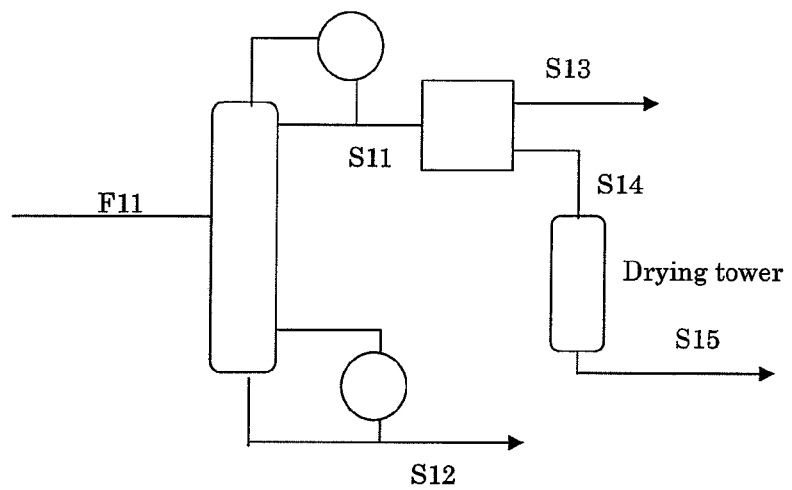
FIG. 3 is a flow chart outlining the steps of the method in Example 3.

Water was removed from 2,3,3,3-tetrafluoropropene according to the flow chart shown in FIG. 3.

First, 2,3,3,3-tetrafluoropropene containing 50 ppm of water was fed to an intermediate tray of a rectification column 2 m in height and 7 cm in diameter at a rate of 10 kg/hr (Stream F11), and rectified under the following conditions: column operating pressure: 0.6 MPa; column top temperature: 21° C.; and reflux ratio: 16.

2,3,3,3-tetrafluoropropene with an increased water content was withdrawn from the top of the column and fed to a decanter at a rate of 1 kg/hr (Stream S11). By cooling to 2° C., liquid-liquid separation was allowed to proceed. The lower layer was withdrawn as a liquid (Stream S14) and dried by being passed through a drying tower containing molecular sieve 4A (Stream S15). The upper layer was isolated as a water-rich layer (Stream S13).

2,3,3,3-tetrafluoropropene with a reduced water content was obtained from the bottom of the column at a rate of 9 kg/hr (Stream S12).

Table 3 below shows the results of measuring the water content of each stream by a Karl Fischer moisture meter.

TABLE 3

| Water content (by weight) | | | | | |
|---|---|---|---|---|---|
| F11 | S11 | S12 | S13 | S14 | S15 |
| 50 ppm | 200 ppm | 3 ppm | 90% | 30 ppm | 5 ppm |

The invention claimed is:

1. A process for producing 2,3,3,3-tetrafluoropropene, comprising distilling a mixture of water and 2,3,3,3-tetrafluoropropene having a water content lower than that of the azeotropic composition thereof by using a distillation column to separate the mixture into a first stream obtained from the top of the column, and a second stream obtained from the bottom of the column, the first stream containing 2,3,3,3-tetrafluoropropene with a water content higher than that of the original mixture, and the second stream containing 2,3,3,3-tetrafluoropropene with a water content lower than that of the original mixture; and obtaining 2,3,3,3-tetrafluoropropene with a reduced water content from the second stream.

2. The process for producing 2,3,3,3-tetrafluoropropene according to claim 1, wherein the distillation is performed at a pressure in the range of atmospheric pressure to 2 MPa.

3. The process for producing 2,3,3,3-tetrafluoropropene according to claim 1, further comprising cooling the mixture of the first stream obtained by the separation in claim 1 so that the mixture separates into a liquid phase A in which the water content is higher than the 2,3,3,3-tetrafluoropropene content and a liquid phase B in which the 2,3,3,3-tetrafluoropropene content is higher than the water content.

4. The process for producing 2,3,3,3-tetrafluoropropene according to claim 3, further comprising recycling the liquid phase B obtained by separation in claim 3 to a distillation column.

5. The process for producing 2,3,3,3-tetrafluoropropene according to claim 2, further comprising cooling the mixture of the first stream obtained by the separation in claim 2 so that the mixture separates into a liquid phase A in which the water content is higher than the 2,3,3,3-tetrafluoropropene content and a liquid phase B in which the 2,3,3,3-tetrafluoropropene content is higher than the water content.

6. The process for producing 2,3,3,3-tetrafluoropropene according to claim 5, further comprising recycling the liquid phase B obtained by separation in claim 5 to a distillation column.

* * * * *